US010222695B2

(12) United States Patent
You (10) Patent No.: US 10,222,695 B2
(45) Date of Patent: Mar. 5, 2019

(54) METHOD FOR MANUFACTURING TRANSPARENT SUBSTRATE AND METHOD FOR MANUFACTURING SURFACE ENHANCED RAMAN SCATTERING SUBSTRATE USING THE SAME

(71) Applicant: KOREA RESEARCH INSTITUTE OF STANDARDS AND SCIENCE, Daejeon (KR)

(72) Inventor: Eun-Ah You, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 15/306,990

(22) PCT Filed: Sep. 25, 2015

(86) PCT No.: PCT/KR2015/010193
§ 371 (c)(1),
(2) Date: Oct. 26, 2016

(87) PCT Pub. No.: WO2017/051957
PCT Pub. Date: Mar. 30, 2017

(65) Prior Publication Data
US 2018/0188646 A1    Jul. 5, 2018

(30) Foreign Application Priority Data
Sep. 24, 2015   (KR) .................. 10-2015-0135434

(51) Int. Cl.
*G03F 7/00* (2006.01)
*B29D 11/00* (2006.01)
(Continued)

(52) U.S. Cl.
CPC ........ *G03F 7/0005* (2013.01); *B29D 11/0074* (2013.01); *G03F 7/039* (2013.01);
(Continued)

(58) Field of Classification Search
CPC .................................................... G03F 7/0005
(Continued)

(56) References Cited

U.S. PATENT DOCUMENTS

| 2001/0046202 A1* | 11/2001 | Tanaka .................. B29C 41/22 369/275.5 |
| 2004/0017534 A1* | 1/2004 | Miki ................. G02F 1/134336 349/143 |

(Continued)

FOREIGN PATENT DOCUMENTS

| CN | 104730059 A | 6/2015 |
| JP | 2015052562 A | 3/2015 |
| KR | 1020130003141 A1 | 1/2013 |

OTHER PUBLICATIONS

Abu Hatab, N. et al., "Surface-Enhanced Raman Spectroscopy Substrates Created via Electron Beam Lithography and Nanotransfer Printing," ACS Nano, vol. 2, No. 2, Jan. 12, 2008, 9 pages.

*Primary Examiner* — Tarifur R Chowdhury
*Assistant Examiner* — Omar H Nixon
(74) *Attorney, Agent, or Firm* — McCoy Russell LLP (57) ABSTRACT

Provided is a method for manufacturing a transparent substrate according to an exemplary embodiment of the present invention including: a) forming a photoresist layer satisfying $D=m*(\lambda/2n)$; b) manufacturing a ring-shaped pattern by exposing the photoresist layer and developing the exposed photoresist layer, using a photo mask including a transparent base and a plate-type metal dot formed contacting a light emitting surface of the transparent base; c) manufacturing a second mold to which the ring-shaped pattern is reversely transferred by using a substrate on which the ring-shaped pattern is formed as a first mold; and d) manufacturing the transparent substrate in which a ring-shaped transparent protrusion is integrally formed with the transparent base by filling a liquefied transparent resin in the second mold and (Continued)

curing the transparent resin and removing the second mold to transfer the ring-shaped pattern.

17 Claims, 5 Drawing Sheets

(51) Int. Cl.
 *G03F 7/039* (2006.01)
 *G03F 7/16* (2006.01)
 *G03F 7/20* (2006.01)
 *G03F 7/26* (2006.01)
 *B29K 75/00* (2006.01)
 *G01N 21/65* (2006.01)

(52) U.S. Cl.
 CPC .............. *G03F 7/16* (2013.01); *G03F 7/2002* (2013.01); *G03F 7/26* (2013.01); *B29K 2075/00* (2013.01); *B29K 2883/00* (2013.01); *G01N 21/658* (2013.01)

(58) Field of Classification Search
 USPC ........................................................ 356/244
 See application file for complete search history.

(56) References Cited

U.S. PATENT DOCUMENTS

| | | | |
|---|---|---|---|
| 2006/0014329 A1* | 1/2006 | Park | B82Y 10/00 438/142 |
| 2006/0199103 A1* | 9/2006 | Neisser | G03F 7/091 430/270.1 |
| 2008/0304397 A1* | 12/2008 | Lee | G03F 7/70383 369/112.27 |
| 2009/0087793 A1* | 4/2009 | Kim | G03F 1/50 430/320 |
| 2009/0134486 A1* | 5/2009 | Fujikata | H01L 31/02240 257/449 |
| 2011/0051142 A1* | 3/2011 | Yanagisawa | G01N 21/554 356/445 |
| 2011/0317160 A1 | 12/2011 | Li et al. | |
| 2012/0071352 A1 | 3/2012 | Liao et al. | |
| 2012/0078523 A1* | 3/2012 | Letant | G01N 21/658 702/19 |
| 2012/0237857 A1* | 9/2012 | Chiu | G03F 1/42 430/5 |
| 2014/0198314 A1 | 7/2014 | Li et al. | |
| 2015/0063748 A1* | 3/2015 | Zhang | G02B 6/1226 385/28 |
| 2015/0152294 A1* | 6/2015 | Sherman | C09J 7/0203 428/200 |

* cited by examiner

METHOD FOR MANUFACTURING TRANSPARENT SUBSTRATE AND METHOD FOR MANUFACTURING SURFACE ENHANCED RAMAN SCATTERING SUBSTRATE USING THE SAME

CROSS-REFERENCE TO RELATED APPLICATIONS

The present application is a U.S. National Phase of International Patent Application Serial No. PCT/KR2015/010193, entitled "METHOD FOR MANUFACTURING TRANSPARENT SUBSTRATE AND METHOD FOR MANUFACTURING SURFACE ENHANCED RAMAN SCATTERING SUBSTRATE USING THE SAME," filed on Sep. 25, 2015. International Patent Application Serial No. PCT/KR2015/010193 claims priority to Korean Patent Application No. 10-2015-0135434, filed on Sep. 24, 2015. The entire contents of each of the above-cited applications are hereby incorporated by reference for all purposes.

TECHNICAL FIELD

The present invention relates to a method for manufacturing a transparent substrate and a method for manufacturing a surface enhanced Raman scattering substrate using the same, and more particularly, to a method for manufacturing a transparent substrate and a method for manufacturing a surface enhanced Raman scattering substrate using the same capable of detecting and analyzing optical characteristics of materials to be analyzed using optical transparency and carrying and fixing and finely arraying heterogeneous materials including nanoparticles.

BACKGROUND ART

A surface enhanced Raman scattering (SERS) spectroscopy is a spectroscopy using a phenomenon that Raman scattering intensity is suddenly increased over $10^6$ to $10^8$ times when molecules are adsorbed to a surface of a metal nano structure such as gold and silver. The SERS spectroscopy is a supersensitive technology that may obtain bulk information by one-time measurement using data of a vector quantity and may directly measure only one molecule and is recognized as a powerful analysis method for chemical/biological/biochemical analysis by directly measuring a vibration state of molecule or information on a molecule structure.

Like Korean Patent Laid-Open Publication No. 2013-0095718, an SERS sensor using nanoparticles has been most generally researched, but an arrangement of metal nanoparticles has a random structure by probability and therefore may not have a defined structure, such that it is difficult to acquire reproducibility and accuracy of the SERS sensor. Further, since it is difficult to make a structure in which a position of a hot spot at which a localized surface plasmon resonance (LSPR) occurs, a density of the hot spot, etc., are defined well, which becomes obstacles to quantitative analysis.

DISCLOSURE

Technical Problem

An object of the present invention is to provide a method for manufacturing a transparent substrate capable of detecting and analyzing optical characteristics of a material to be analyzed using optical transparency, and more particularly, to a method for manufacturing a transparent substrate that may define a physical structure to implement reproducibility and reliability and may be used as a surface enhanced Raman scattering substrate accurately controlling a position which a hot spot is generated and a density of the hot spot and a method for manufacturing a surface enhanced Raman scattering substrate using the same.

Technical Solution

In one general aspect, a method for manufacturing a transparent substrate includes: a) forming a photoresist layer satisfying the following Relational Expression 1 on a substrate; b) manufacturing a ring-shaped pattern by exposing the photoresist layer and developing the exposed photoresist layer, using a photo mask including a transparent base and a plate-type metal dot formed contacting a light emitting surface of the transparent base; c) manufacturing a second mold to which the ring-shaped pattern is reversely transferred by using a substrate on which the ring-shaped pattern is formed as a first mold; and d) manufacturing the transparent substrate in which a ring-shaped transparent protrusion is integrally formed with a transparent base by filling a liquefied transparent resin in the second mold and curing the transparent resin and removing the second mold to transfer the ring-shaped pattern.

$$D = m*(\lambda/2n) \quad \text{(Relational Expression 1)}$$

(D is a thickness of the photoresist layer, n is a refractive index of the photoresist, λ is a wavelength of light irradiated at the time of exposure, and m is a natural number of 1 or more).

In the step b), the photo mask may satisfy the following Relational Expression 2 and an interval between the photo mask and the photoresist layer may satisfy the following Relational Expression 3.

$$150 \text{ nm} \leq R \leq 1.5 \text{ μm} \quad \text{(Relational Expression 2)}$$

(In the above Relational Expression 2, R is a radius of the plate-type metal dot)

$$\text{Gap} \leq 200 \text{ nm} \quad \text{(Relational Expression 3)}$$

(In the above Relational Expression 3, Gap may be a spaced distance between the photo mask and the photoresist layer).

In the step b), a ring-shaped pattern in which an outer diameter of the ring is 70% to 200% with respect to the metal dot diameter, an inner diameter thereof is 5 to 80% with respect to the metal dot diameter, and a width of the ring is 2 to 48% with respect to the metal dot diameter may be manufactured by using the photo mask formed with the plate-type metal dot having a diameter of 300 nm to 3 μm.

The second mold may be a siloxane-based elastomeric polymer.

The transparent substrate may be polyurethane.

In the step d), the ring-shaped pattern in which a bottom surface inside the ring of the transparent protrusion is concavely curved may be manufactured.

In the step b), the ring-shaped pattern may be a single-layered ring shape and a multi-layered ring shape in which at least two rings are stacked, each ring of the multi-layered ring shape may have a concentric structure, and an upper ring may be positioned in a lower ring, in consideration of a projection image in a light irradiation direction.

In the step b), metal of the plate-type metal dot may be at least one selected from transition metals including Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, and Au, post-transition metals including Al, Ga, In, Tl, Sn, Pb, and Bi, and metals including Li, Be, Na, Mg, K, Ca, Rb, Sr, Cs, and Ba.

In the step b), light irradiated at the time of the exposure may be ultraviolet (UV) rays and may be irradiated at a dose of 90 to 110 mJ/cm$^2$.

In another general aspect, a method for manufacturing a surface enhanced Raman scattering substrate includes: positioning metal nanoparticles generating surface plasmons in a ring of a ring-shaped transparent protrusion of the transparent substrate manufactured by the method for manufacturing a transparent substrate as described above.

In the ring-shaped transparent protrusion, a bottom surface inside the ring may have a concavely curved shape and a hot spot may be formed by physically contacting metal nanoparticles by the curved shape of the bottom surface.

A surface of the metal nanoparticles may be formed with an acceptor that is specifically bonded to a material to be detected.

The positioning of the metal nanoparticles may include dipping the transparent substrate in a dispersion in which the metal nanoparticles are dispersed.

Upon the dipping, an angle between the transparent substrate and a surface of the dispersion may be maintained at 0 to 60°.

In another general aspect, a surface enhanced Raman scattering substrate includes: a transparent base having a transparent plate shape and an array in which a ring-shaped transparent protrusions integrated with the transparent base are arranged to be spaced apart from each other, wherein the inner diameter of the ring shape ranges from 300 nm to 2 μm and the metal nanoparticles generating surface plasmons are positioned in the ring.

In the ring-shaped transparent protrusion, a bottom surface inside the ring may have a concavely curved shape and a hot spot may be formed by physically contacting metal nanoparticles by the curved shape of the bottom surface.

In the transparent protrusion of the array, the same number of metal nanoparticles may be positioned in the ring.

The number of metal nanoparticles positioned in the ring of the transparent protrusion may be 2 to 6.

A surface of the metal nanoparticles may be formed with an acceptor that is specifically bonded to a material to be detected.

Advantageous Effects

The method for manufacturing a transparent substrate according to the exemplary embodiments of the present invention may use the plate-type transparent base and the extremely simple photo mask called the plate-type metal dot to implement the patterning having the sophisticated shape like the micro ring pattern. Therefore, it is possible to pattern the ring using the cheap photo mask without using the expensive PSM mask or the expensive equipment.

Further, the method for manufacturing a transparent substrate according to the exemplary embodiments of the present invention may manufacture the ring pattern having the size smaller than that of the plate-type metal dot and manufacture the ring pattern having various shapes by controlling the dose of irradiated light or the development time using the same photo mask.

In addition, the method for manufacturing a transparent substrate according to the exemplary embodiments of the present invention may be utilized without changing the existing constructed photolithography process by using the exposure apparatus, the exposure method, the photoresist, the developer, and the developing method typically used, except for the mask.

Further, the method for manufacturing a transparent substrate according to the exemplary embodiments of the present invention may manufacture the transparent substrate in which the transparent micro wells capable of carrying and fixing the heterogeneous materials are integrally formed with the transparent base and may manufacture the transparent substrate that may detect and analyze the optical characteristics of the materials to be analyzed using the optical transparency, improve the analysis efficiency using the micro well array by allowing each of the extremely micro wells to provide the independent analysis space, and requires an extremely small quantity of sample for analysis.

The surface enhanced Raman scattering substrate according to the exemplary embodiments of the present invention may have the structure in which the metal nanoparticles in which the surface plasmon is generated is carried in the micro wells to define the kind, density, etc., of the hot spot, thereby making the reproducibility and reliability excellent and performing the quantitative analysis.

DESCRIPTION OF DRAWINGS

The above and other objects, features and advantages of the present invention will become apparent from the following description of preferred embodiments given in conjunction with the accompanying drawings, in which.

BEST MODE

Hereinafter, a method for manufacturing a transparent substrate, a method for manufacturing a surface enhanced Raman scattering substrate, and a surface enhanced Raman scattering substrate according to an exemplary embodiment of the present invention will be described below with reference to the accompanying drawings. The accompanying drawings to be provided below are provided by way of example so that the idea of the present invention can be sufficiently transferred to those skilled in the art to which the present invention pertains. Therefore, the present invention is not limited to the accompanying drawings provided below, but may be modified in many different forms. In addition, the accompanying drawings suggested below will be exaggerated in order to clear the spirit and scope of the present invention. Technical terms and scientific terms used in the present specification have the general meaning understood by those skilled in the art to which the present invention pertains unless otherwise defined, and a description for the known function and configuration unnecessarily obscuring the gist of the present invention will be omitted in the following description and the accompanying drawings.

As a performance result of a study for forming a micro ring-shaped pattern using photolithography, the present applicant surprisingly found that a single-layered or a multi-layered ring pattern may be formed even by a mask having an extremely simple structure in which a plate-type metal dot is formed on a light emitting surface of a plate-type transparent base without artificial surface ruggedness and found that the ring pattern having an outer diameter smaller than a diameter of a plate-type metal dot may be manufactured. As a result of deepening the study, the present applicant found that a transparent substrate in which micro wells for carrying and fixing heterogeneous materials are integrally formed with a base may be manufactured when the transparent substrate to which a micro ring pattern is transferred is manufactured by using a photoresist pattern as a mold using a transparent resin and found that a surface enhanced Raman scattering substrate having excellent reproducibility and reliability and capable of implementing quantitative analysis may be manufactured by accurately controlling a position and a density at which a hot spot is generated upon the use of the micro wells, and thus filed the present invention.

A method for manufacturing a transparent substrate according to an exemplary embodiment of the present invention includes: a) forming a photoresist layer satisfying the following Relational Expression 1 on a substrate; b) manufacturing a ring-shaped pattern by exposing the photoresist layer and developing the exposed photoresist layer, using a photo mask including a transparent base and a plate-type metal dot formed contacting a light emitting surface of the transparent base; c) manufacturing a second mold to which the ring-shaped pattern is reversely transferred by using a substrate on which the ring-shaped pattern is formed as a first mold; and d) manufacturing the transparent substrate in which a ring-shaped transparent protrusion is integrally formed with a transparent base by filling a liquefied transparent resin in the second mold and curing the transparent resin and removing the second mold to transfer the ring-shaped pattern.

$$D=m*(\lambda/2n) \quad \text{(Relational Expression 1)}$$

In the above Relational Expression 1, D is a thickness of the photoresist layer, n is a refractive index of the photoresist, λ is a wavelength of light irradiated at the time of the exposure, and m is a natural number of 1 or more.

Since the steps a) and b) are the manufacturing of the first mold, the step c) is the manufacturing of the second mold, and the step d) is the manufacturing of the transparent substrate using the second mold, the manufacturing of the first mold, the manufacturing of the second mold, and the manufacturing of the transparent substrate will be separately described below.

Manufacturing of First Mold

The manufacturing of the first mold includes: a) forming the photoresist layer satisfying the following Relational Expression 1 on the substrate; and b) manufacturing the ring-shaped pattern by exposing the photoresist layer and developing the exposed photoresist layer using the photo mask including the transparent base and the plate-type metal dot formed contacting the light emitting surface of the transparent base.

$$D=m*(\lambda/2n) \quad \text{(Relational Expression 1)}$$

In the above Relational Expression 1, D is a thickness of the photoresist layer, n is a refractive index of the photoresist, λ is a wavelength of light irradiated at the time of the exposure, and m is a natural number of 1 or more.

The thickness of the photoresist layer satisfying the conditions of the above Relational Expression 1 is set to form a standing wave in a thickness direction of the photoresist layer by resonance of the light irradiated at the time of exposure.

By satisfying the above Relational Expression 1, the photoresist pattern having a single-layered ring shape or the photoresist pattern having a multi-layered ring shape in which a plurality of rings are stacked may be manufactured and the photoresist pattern having a stacked ring shape in which a plurality of rings having a similar or equal thickness are stacked may also be manufactured.

The photoresist coated on the base may include a photosensitive resin. As the photosensitive resin, any polymer material may be used as long as it has resistance against chemical changed due to light used in a typical lithography process. The photoresist may be a positive type photosensitive resin which becomes soluble for chemicals or a negative type photosensitive resin which becomes insoluble for chemicals, by being exposed to light. That is, the photoresist coated on the base may be a positive photoresist or a negative photoresist.

The thickness of the photoresist coated on the substrate needs to satisfy the above Relational Expression 1, in which the m which is a natural number may be a natural number in which a thickness D of the photoresist ranges from 50 nm to 500 nm. This causes a risk that when the thickness of the photoresist is too thin as less than 50 nm, the thickness of the photoresist remaining while being patterned in the ring form on the base is too thin, and therefore physical stability of a transparent well (transparent protrusion) manufactured may be reduced. Further, when the thickness of the photoresist coated on the base is too thick exceeding 500 nm, a too large surface step is formed on the base by the photoresist, and thus badness may occur upon the manufacturing of the second mold using the first mold.

To effectively perform the mold role without degrading the quality of the subsequent processes, and prevent a yield from being unwantedly reduced, the m which is a natural number of the above Relational Expression 1 is more preferably a natural number in which the thickness D of the photoresist ranges from 200 to 500 nm. As described above, considering the wavelength (central wavelength) of the irradiated light and the refractive index of the photoresist, the natural number m may be appropriately set to have the desired thickness of the photoresist as described above. Considering a wavelength of ultraviolet light used in the typical photolithography process and the typical refractive index of photoresist, as a detailed and non-resistive example, m may range from 2 to 7. In this case, in the above Relational Expression 1, the thickness D of the photoresist layer means a thickness within an error range which may occur during the typical photoresist forming processes such as coating and drying a photosensitive resin solution, soft baking, and hard baking. The thickness (average thickness) within the error range may range from 0.9% to 1.1% of the D suggested in the above Relational Expression 1, in detail, 0.95% to 1.05%.

In the manufacturing of the first mold, the photo mask satisfies the following Relational Expression 2 and an interval between the photo mask and the photoresist layer may satisfy the following Relational Expression 3, specifically, the following Relational Expression 3-1.

$$150 \text{ nm} \leq R \leq 1.5 \text{ µm} \qquad \text{(Relational Expression 2)}$$

In the above Relational Expression 2, R is a radius of the plate-type metal dot.

$$\text{Gap} \leq 200 \text{ nm} \qquad \text{(Relational Expression 3)}$$

In the above Relational Expression 3, Gap is a spaced distance between the photo mask and the photoresist layer.

$$50 \text{ nm} \leq \text{Gap} \leq 200 \text{ nm} \qquad \text{(Relational Expression 3-1)}$$

In the above Relational Expression 3-1, a gap is a spaced distance between the photo mask and the photoresist layer.

The above Relational Expressions 2 and 3 are conditions under which the photoresist pattern having a shape corresponding to the plate-type metal dot but having a hollow ring shape may be manufactured.

In detail, as suggested in the above Relational Expression 2, when a maximum radius of the plate-type metal dot exceeds 1.5 µm or a minimum radius of the plate-type metal dot is less than 150 nm, the photoresist pattern having the desired ring shape may not be likely to be manufactured by the exposure and the development.

To manufacture the pattern having the ring shape as the shape well corresponding to the shape of the plate-type metal dot, the radius of the plate-type metal dot may more preferably range from 300 to 700 nm.

In this case, the thickness of the plate-type metal dot is set to be a thickness enough to prevent the light irradiated at the time of the exposure from being transmitted. As a detailed and non-restrictive example, the thickness of the plate-type metal dot may range from 50 nm to 150 nm.

As described above, it is preferable to form an extremely micro gap satisfying the above Relational Expression 3 between the photo mask and the photoresist, while satisfying the above Relational Expression 2.

The photoresist layer has a thickness satisfying the above Relational Expression 1 and is formed with an air layer (spaced distance, gap) which is equal to or less than 200 nm satisfying the above Relational Expression 3, along with the plate-type metal dot satisfying the above Relational Expression 2, such that a light concentration area in which light is concentrated on a center of the metal dot may be formed and a plurality of light concentration areas spaced apart from each other in the thickness direction of the photoresist may be formed.

Therefore, the photoresist layer satisfying the above Relational Expression 1 is formed with a nano air gap satisfying the above Relational Expression 3 using the photo mask formed with the plate-type metal dot satisfying the above Relational Expression 2, such that when the exposure is performed, the pattern having the single-layered ring shape and the pattern having the stacked ring shape in which the plurality of rings are stacked on each other may also be manufactured.

In detail, in the case of satisfying the above Relational Expressions 1, 2, and 3, by setting a direction from a surface to which light is irradiated in the photoresist layer to a interphase contacting the substrate in the photoresist layer as a depth direction, the photoresist layer is formed with a first standing wave in which light is repeatedly concentrated and extinct along the depth direction at the time of the exposure, as the shape corresponding to the shape of the plate-type metal dot at areas corresponding to edges of the plate-type metal dot, and at the same time may be formed with a second standing wave in which light is repeatedly concentrated and extinct along the depth direction at an area corresponding to a center of the plate-type metal dot, in which a phase difference between the first standing wave and the second standing wave may be set to be 180°. That is, due to the phase difference of 180°, the concentration of light of the second standing wave occurs at the thickness of the photoresist at which the extinction of light of the first standing wave occurs.

A manufacturing method according to an exemplary embodiment of the present invention may manufacture the photoresist pattern having the stacked ring shape in which the single-layered ring-shaped rings or the plurality of rings are stacked in the thickness direction by forming the above-mentioned first standing wave and second standing wave on the photoresist layer, based on the above Relational Expressions 1, 2, and 3.

That is, according to the manufacturing method according to the exemplary embodiment of the present invention, the photoresist pattern acquired by the exposure and the development may be the single-layered ring shape or the multi-layered ring shape in which at least two rings are stacked. In this case, as described above, in the ring shape, both of a shape of an empty air gap which is an inside shape and a shape of an edge which is an outside shape may have a shape corresponding to the plate-type metal dot.

Further, in the manufacturing method according to the exemplary embodiment of the present invention, when the exposure is performed to satisfy the above Relational Expression 3 by using the photo mask of the above Relational Expression 2, the second standing wave proceeds in parallel with the thickness direction and the larger the thickness direction, the narrower the width (width in a vertical direction to a depth direction) in the area in which the light is concentrated. At the same time, the first standing wave has a phase difference of 180° with respect to the second standing wave and the lager the thickness direction, the wider the width of the area in which the light is extinct. The width of the area in which the light of the second standing wave is concentrated may affect an inner diameter of the ring shape and the width of the area in which the light of the first standing wave is extinct may affect an outer diameter of the ring.

Therefore, by the above-mentioned first standing wave and second standing wave, the photoresist pattern having the stacked ring shape in which the plurality of rings having a concentric structure and having the outer diameter reduced upwardly (surface side to which light is irradiated) and the inner diameter increased upwardly are stacked may be manufactured. That is, in the photoresist pattern having the multi-layered ring shape, each ring forming the multi-layered ring has the concentric structure and an upper ring may be positioned in a lower ring, based on a projection image of multi-layered ring shape in a light irradiation direction.

That is, when a difference between the outer diameter and the inner diameter of one ring is the width of the ring, the rings are stacked while forming the multi-layered ring shapes having the same concentric structure to each other, and the photoresist pattern having the multi-layered ring shape in which the rings in which the width of the ring positioned at the relatively upper portion (surface side to which light is irradiated) is narrower (smaller) than the width of the ring positioned at the relatively lower portion (substrate side) are stacked forming concentricity may be manufactured.

The more surprising fact is that when the exposure is performed under the condition that the nano gap satisfying the above Relational Expression 3 between the mask and the photoresist is formed by using the mask in which the extremely micro plate-type metal dot satisfying the above Relational Expression 2 is formed, the pattern having the extremely micro ring shape having the outer diameter smaller than the plate-type metal dot may be manufactured.

In detail, the outer diameter of the at least upper ring having the multi-layered ring shape may be smaller than the diameter of the metal dot. In this case, the outer diameter of the upper ring means a ring other than the bottom ring contacting the substrate, that is, a ring positioned at the upper portion of the bottom ring in the stacked ring in which at least two rings are stacked.

In more detail, the manufacturing method according to the exemplary embodiment of the present invention may manufacture the ring pattern having the outer diameter of the ring which is about 70% of the diameter of the plate-type metal dot. In detail, in the stacked ring shape, the photoresist pattern having the stacked ring shape in which the outer diameter of the upper ring including at least the top reaches 70% to 96% based on the diameter of the metal dot, in detail, 70% to 85% may be manufactured.

The photoresist pattern having the single-layered ring shape or the multi-layered ring shape may be controlled by at least one factor selected from the dose of light irradiated at the time of the exposure and the development time.

In detail, the photoresist pattern having the single-layered ring shape or the multi-layered ring shape may be manufactured by controlling the dose of light irradiated at the time of the exposure.

When the dose of irradiated light is increased over a predetermined dose, the light concentration areas of the first standing wave may be coupled with each other. In this case, a boundary between the light concentration areas is unclear and the single-layered ring pattern may be manufactured.

That is, when light is irradiated at a dose high enough to couple between the light concentration areas of the first standing wave in the thickness direction, the single-layered ring pattern may be manufactured, while light is irradiated at s low dose so that the light concentration area and a light extinction area is alternately formed in the thickness direction of the photoresist layer, such that the multi-layered ring pattern may be manufactured.

The dose at the boundary at which the multi-layered ring pattern and the single-layered ring pattern are formed may be changed to some extent, in consideration of a kind, development conditions, etc., of the photoresist. However, to stably manufacture the multi-layered ring pattern, it is preferable to irradiate a dose of 110 mJ/cm$^2$ or less, in more stably, 105 mJ/cm$^2$ or less.

In this case, the dose of light irradiated at the time of the exposure needs to be a dose high enough to expose the photoresist layer (that is, exposure may be performed up to the bottom surface of the photoresist which is a surface contacting a substrate). In this regard, the dose of light irradiated at the time of the exposure may be a minimum of 90 mJ/cm$^2$, preferably, 95mJ/cm$^2$ or more.

As described above, in the case of manufacturing the photoresist pattern having the single-layered ring shape or the multi-layered ring shape, the dose of irradiated light may be 90 to 110 mJ/cm$^2$, preferably, 95 to 105 mJ/cm$^2$. When the photoresist pattern having the single-layered ring shape is manufactured substantially independent of the development time due to the dose of irradiated light, light having a dose of light irradiated at the time of the exposure which exceeds 110 mJ/cm$^2$, more stably, 115 mJ/cm$^2$ or more may be irradiated. As a detailed example, to manufacture the photoresist pattern having the single-layered ring shape, light having a dose of 115 to 200 mJ/cm$^2$, preferably, 120 to 200 mJ/cm$^2$ may be irradiated.

Further, even when the exposure is performed at the dose (predetermined dose) at which the multi-layered ring may be formed, the single-layered ring pattern or the multi-layered ring pattern may be selectively manufactured by controlling the development time.

This means that even when the exposure is performed at a predetermined dose at which the multi-layered ring is formed, the development may be performed for a relatively longer period of time enough to remove the coupled portion between the photoresist region corresponding to the upper ring and the photoresist region corresponding to the lower ring by the development to manufacture the single-layered ring pattern and also means that the development may be performed for a relatively shorter period of time enough not to remove the coupled portion between the photoresist region corresponding to the upper ring and the photoresist region corresponding to the lower ring by the development to manufacture the multi-layered ring pattern.

The development time may be properly changed in consideration of a kind of the photoresist, a kind of developer used for the development, etc. As a detailed example, when intending to manufacture the multi-layered ring shape, the development may be performed for 10 to 100 seconds and when intending to manufacture the single-layered ring shape, the development may be performed for 100 seconds or more, stably, 150 seconds or more.

Like the preferred example to be described below, in the case of the transparent substrate and the Raman scattering substrate using the same according to the embodiment of the present invention, a bottom surface inside the ring has a concavely curved shape, such that the well defined, stably and reproducibly physical contact between the metal nanoparticles may be formed. In connection with the manufacturing of the ring-shaped pattern in which the bottom surface inside the ring is concavely curved, each ring has a concentric structure and a multi-layered ring shape in which an upper ring is positioned in a lower ring based on the projection image in a light irradiation direction may be more advantageous. The reason is that each ring forming the multi-layered ring has a concentric structure but as the ring positioned at a lower portion (that is, as the ring approaches the substrate on which the photoresist is coated) has a smaller inner diameter, a pattern of which the inside is concave on the whole is manufactured.

In the manufacturing method according to the exemplary embodiment of the present invention, prior to the exposing, the forming of the photoresist layer to satisfy the above Relational Expression 1 by coating the photoresist on the substrate may be performed. In this case, the substrate serves as a support and is coupled with lower portions of protrusions at the transparent substrate to be manufactured to be transferred to a transparent plate integrally formed with the protrusions.

The substrate may be a wafer or film shape, and may be a laminate in which semiconductor, ceramic, metal, polymer or at least two materials selected therefrom are stacked while forming each layer. A non-restrictive example of the semiconductor substrate may include a laminate in which IV semiconductor including silicon (Si), germanium (Ge), or silicon germanium (SiGe), III-V semiconductor including gallium arsenic (GaAs), indium phosphorus (InP), or gallium phosphorous (GaP), II-VI semiconductor including cadmium sulfide (CdS) or zinc telluride (ZnTe), IV-VI semiconductor including lead sulfide (PbS), or at least two selected therefrom is stacked while forming each layer.

As described above, the photoresist may be a positive type or a negative type and after the photoresist is coated on the substrate using the typical processes including spin coating, etc., the drying (soft baking) of the coated layer may be performed and the hard baking may be selectively performed. In this case, a heterogeneous layer is preferable not to be formed on the photoresist layer so that the photoresist layer directly faces the photo mask through the air gap.

The exposing may be performed by positioning the photo mask between the light source and the substrate on which the photoresist layer is formed and then irradiating light so that the transparent base side at which the plate-type metal dot is positioned is the light emitting surface.

As described above, the photo mask may include the transparent base and the plate-type metal dot. By the advantages of the present invention as described above, the photo mask may be configured of the transparent base and the plate-type metal dot or may be configured of the transparent base, the plate-type metal dot, and a protruding member to be described below.

In the transparent base, light is incident on one surface of two opposite surfaces of the transparent base and is emitted from the other surface thereof. According to the exemplary embodiment of the present invention, at least a light emitting surface of the transparent base may be a flat plane and may be a transparent plate shape in which both of a light incident surface and a light emitting surface are flat.

The transparent base may be made of a material enough to be used as a substrate through which light is transmitted in the typical photo mask for photolithography. For example, the transparent base may be made of quartz, but the present invention is not limited thereto.

The transparent base may have a typical thickness enough to transmit light through the mask in the typical physical photo mask for photolithography. For example, the thickness of the transparent base may range from several μm to tens of mm, but the present invention is not limited thereto.

The plate-type metal dot may be positioned on the light emitting surface of the transparent base while contacting the transparent base. When the exposure and the development of the photoresist are performed using the photo mask, the ring pattern having a shape corresponding to a contour (shape of an edge) of the plate-type metal dot may be manufactured.

In detail, the plate-type metal dot may have at least one shape selected from a circular shape, an oval shape, and a polygonal shape. In this case, the polygonal shape includes a triangle to an octagon, in detail, a triangle, a quadrangle (rectangle or square), a pentagon, a hexagon, a heptagon, or an octagon. Therefore, it is possible to pattern a circular ring, an oval ring, or a polygonal ring of a triangle to an octagon.

Further, the photo mask be one that at least two plate-type metal dot are arranged on the light emitting surface of the transparent base. The arrangement of the plate-type metal dot may include a regular arrangement or an irregular arrangement and the arrangement of the plate-type metal dot may be properly controlled in consideration of the designed structure to be patterned within a range in which the optical interference between the plate-type metal dots does not occur.

The metal of the plate-type metal dot may be at least one selected from transition metals including Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, and Au, post-transition metals including Al, Ga, In, Tl, Sn, Pb, and Bi, and metals including Li, Be, Na, Mg, K, Ca, Rb, Sr, Cs, and Ba. In detail, the metal of the plate-type metal dot may be at least one or two selected from transition metals including Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, and Au. In more detail, the metal of the plate-type metal dot may be Cr.

In this case, the photo mask may further include the protruding member so that the nano gap (air gap) depending on the above Relational Expression 3 is stable in a region which does not affect the patterning of the photoresist layer, for example, an edge region of the transparent base and is formed at a preset value.

As the protruding member serves to control a spaced distance between the photo mask and the photoresist layer (Gap=distance between the photo mask and the photoresist layer=distance between the plate-type metal dot and the photoresist layer), a height of the protruding member may be a value obtained by summing the height of the plate-type metal dot formed on the photo mask and the gap depending on the Relational Expression 3. Due to the foregoing protruding member, the size of the air gap may be controlled precisely and reproducibly by a simple method for adhering the photo mask to the photoresist.

To satisfy the Relational Expression 3, after the photo mask is aligned on the photoresist layer, as described above, the exposure may be performed by irradiating light at the dose of at least 90 mJ/cm$^2$.

In this case, the irradiated light may be ultraviolet (UV) and may be ultraviolet having a wavelength band of 10 nm to 500 nm. In detail, a central wavelength of the irradiated light may range from 300 nm to 500 nm, in more detail, 350 to 380 nm, 400 to 420 nm, and/or 420 to 450 nm. That is, the manufacturing method according to the exemplary embodiment of the present invention may perform the exposure using ultraviolet including wavelengths of I-line, H-line, and/or G-line typically used in the existing photolithography process. Further, in the exposing, light may be irradiated using the optical means typically used in the photolithography process. This means that in the manufacturing of the first mold, the photoresist, the exposing apparatus, etc., that are typically used in the existing photolithography process other than the photo mask may be used as they are.

The developing may be performed by the developer and the development method which are typically used in the photolithography process. As the detailed example of using the positive type photoresist, the developing may be performed by removing a photosensitive resin portion of which the chemical characteristics are changed by using the developer containing a solvent which melts and removes the photosensitive resin portion of which the chemical characteristics are changed by the exposure.

In the case of using the foregoing manufacturing method, by using the photo mask in which the plate-type metal dot having a diameter of 300 nm to 3 μm is formed, the ring pattern in which the outer diameter of the ring is 70% to 200% based on the metal dot diameter and the inner diameter thereof is 5 to 80% with respect to the metal dot diameter may be manufactured and the ring pattern in which a width of the ring is 2 to 48% with respect to the metal dot diameter may be manufactured.

Manufacturing of Second Mold

The manufacturing of second mold may include manufacturing the second mold to which the ring-shaped photoresist pattern is reversely transferred by using the substrate on which the ring-shaped photoresist pattern is formed as the first mold.

The second mold to which the ruggedness of the first mold is reversely transferred may have a ruggedness of a concave part and a convex part having a complementary dimension and shape to a convex part and a concave part forming a ring-shaped ruggedness based on the surface of the substrate on which the ring-shaped photoresist pattern is formed.

In the manufacturing of the second mold, the second mold may be manufactured by coating a polymer having hardenability (hereinafter, curable polymer) on the first mold and then hardening the polymer and separating the first mold.

As the curable polymer, any polymer may be used as long as it secures mechanical and physical strength while having elasticity to facilitate the physical secession (separation) between the first mold and the second mold and is rarely changed in the volume upon hardening, any polymer may be used. The curable polymer may be a photo curable polymer, a thermal curable polymer, or a chemical curable polymer, but is not limited thereto. Therefore, changing a liquefied polymer resin to a solid state by the volatile removal of a solvent dissolving the polymer resin may also be interpreted as hardening.

In detail, the curable polymer may be a siloxane-based polymer, an olefin-based elastomeric polymer, or a polyurethane-based compound having high flexibility and elasticity after the hardening.

Preferably, the curable polymer may be the siloxane-based polymer and the second mold may be a siloxane-based elastomeric polymer. The siloxane-based elastomeric polymer has very high flexibility and elasticity and therefore is not easily damaged even by the physical deformation, such that it is suitable for a mold material. Further, as known, as sharp corners of the transferred ruggedness are rounded by high elasticity when the siloxane-based elastomeric polymer is used as the mold, it is advantageous to manufacture the ring shape having a concavely curved bottom surface. To effectively round the sharp corners, a modulus of elasticity (25° C., modulus of elasticity upon tension, ASTM D412) of the siloxane-based elastomeric polymer ranges from 0.5 to 50 MPa, preferably, 1 to 20 MPa. As the siloxane-based polymer any material may be used as long as it may prepare the siloxane-based elastomeric polymer having the foregoing elasticity by the hardening. As the detailed example, the siloxane-based polymer may be polysiloxane including a siloxane repeating unit in which aliphatic polysiloxane, aromatic polysiloxane, or an aliphatic group and an aromatic group all are included in one repeating unit or they each are independently included. As one non-restrictive detailed example, the aliphatic polysiloxane may be selected from polydimethylsiloxane, polydiethyl siloxane, polymethylethyl siloxane, polydimethylsiloxane-co-diethylsiloxane, polydimethylsiloxane-co-ethylmethylsiloxane, and the like and the aromatic polysiloxane may be selected from polydiphenylsiloxane, a polymethylphenylsiloxane, polyethylphenylsiloxane, poly (dimethylsiloxane-co-diphenylsiloxane), and the like. The polysiloxane including the siloxane repeating unit in which the aliphatic group and the aromatic group all are included in one repeating unit or they each are independently included includes both of the repeating unit of the aliphatic siloxane and the repeating unit of the aromatic siloxane that are exemplified above or means the form in which the aliphatic substituent and the aromatic substituent that are exemplified above are each bonded to a silicon element positioned within one repeating unit, but is not limited thereto. As the more detailed example of the siloxane-based polymer, any polymer may be used as long as it prepares the siloxane-based elastomeric polymer typically used in a field of transferring a micro pattern by soft-lithography. An example of a commercial product may include Sylgard® 184 of Dow Corning or the like, but the commercial product is not limited thereto.

The curable polymer may be a liquefied material, in detail, the curable polymer itself may be a liquid phase or a solution phase dissolved in a solvent.

After the hardening of the curable polymer coated on the first mold is performed, the cured polymer resin and the first mold are separated from each other, and as a result the second mold may be manufactured. The separation may be performed by the application of a physical force, chemical etching, or the like and the present invention may not be limited to the separation method between the molds.

Manufacturing of Transparent Substrate

The manufacturing of the transparent substrate may include manufacturing the transparent substrate in which the ring-shaped transparent protrusion is integrally formed with the transparent base by coating the liquefied transparent resin on the manufactured second mold and hardening the transparent resin, removing the second mold, and then transferring the ring-shaped pattern of the first mold.

The transparent resin may mean a resin through which visible light or light in a near infrared ray region is transmitted when being hardened, in detail, resin in which light transmittance of a wavelength band ranging from 0.4 µm to 3 µm is equal to or more than 95%.

As the transparent resin, any resin may be used as long as it satisfies the foregoing optical characteristics and has hardenability. An example of the resin may be at least one selected from acrylic resin, polycarbonate resin, acrylonitrile butadiene styrene resin, polyurethane resin, olefin-based resin, epoxy-based resin, melamine-based resin, and unsaturated polyester-based resin. In this case, the hardenability may be photo hardenability including ultraviolet rays (UV), thermal hardenability, or chemical hardenability, preferably, UV hardenability.

Preferably, the transparent substrate is made of polyurethane having excellent elasticity and flexibility like the second mold that is the siloxane-based elastomeric polymer, while having the foregoing optical transparency. In this case, the sharp corner may be more effectively rounded by a surface tension generated by the elasticity along with the second mold, and as a result it is advantageous to manufacture the ring-shaped protrusion having a smoothly curved bottom surface.

In more detail, the second mold is the foregoing siloxane-based elastomeric polymer and the transparent substrate may be made of high-elastic polyurethane in which a modulus of elasticity (25□ C., modulus of elasticity upon tension, ASTM D412) ranges from 50 to 1500 MPa. As the transparent resin, any resin may be used as long as it prepares the polyurethane having the foregoing elasticity by hardening (polymerization). As the detailed example, the transparent resin may include a multi-functional isocyanate-based compound containing at least two isocyanate groups and a polyol-based compound containing at least two hydroxy groups and may be hardened by an additional condensation reaction of the isocyanate group (—NCO) and the hydroxy group (—OH). As another example, the transparent resin may include a polyurethane-based pre-polymer containing an unsaturated group and a cross-linker and may be hardened by an additional reaction of the pre-polymer and the cross-linker. As one non-restrictive detailed example, the multi-functional isocyanate-based compound may include 4,4'-diphenylmethane diisocyanate (MDI), toluene diisocyanate (TDI), 1,4-diisocyanatebenzene (PPDI), 2,4'-diphenylmethane diisocyanate, 1,5-naphthalene diisocyanate, 3,3'-bitolylene 4,4'-diisocyanate, 1,3-xylene diisocyanate, p-tetramethylxylene diisocyanate (p-TMXDI), 1,6-diisocyanate-2,4,4-trimethylhexane, hexamethylene diisocyanate (HMDI) 1,4-cyclohexane diisocyanate (CHDI), isophorone diisocyanate (IPDI), 4,4'-dicyclohexyl methane diisocyanate (H12MDI), or the like, but is not limited thereto. The polyol-based compound may be divided into polyester polyol and polyether polyol. As one non-restrictive detailed example, the polyester polyol may be polyethyleneadipate, polybutyleneadipate, poly(1,6-hexaadipate), polydiethylene adipate or poly (e-caprolactone), and the like and as one non-restrictive detailed example, the polyether polyol may be polyethyleneglycol, polydiethyleneglycol, polytetramethyleneglycol, polyethylenepropyleneglycol, and the like, but they are not limited thereto. The polyurethane pre-polymer may have various structures according to a kind of compounds including an isocyanate group and the polyol-based compound and may be the ethylenical unsaturated group, in detail, the polyurethane-based pre-polymer including the vinyl group. As one detailed example, 2 to 20 vinyl groups may be included in one polyurethane chain but the number of vinyl groups is not limited thereto. Therefore, as a molecular weight of the polyurethane is increased, the number of vinyl groups may be increased to exceed 20 in proportion to the increase in the molecular weight. In the case of the polyurethane having a low molecular weight, the number of vinyl groups may preferably range from 2 to 4. In this case, the cross-linker may be a vulcanizing agent and any cross-linker generally used in the art may be used without any limitation. As one detailed example, a sulfur containing organic material, organic peroxide, or the like may be used.

The transparent resin may be a liquefied material, in detail, the transparent resin itself may be a liquid phase or a solution phase dissolved in a solvent.

The transparent substrate may be manufactured by coating (filling) a liquefied transparent resin on the second mold and hardening the transparent resin and then detaching the second mold. In this case, to promote the physical stability of the transparent substrate, the liquefied transparent resin is coated on the second mold, the transparent support like glass is stacked on the coated transparent resin, and then the liquefied transparent resin may be hardened.

After the transparent resin coated (filled) in the second mold is hardened, the hardened transparent resin and the second mold are separated from each other, and as a result the transparent substrate may be manufactured. The separation may be performed by the application of the physical force, the chemical etching, or the like but is not limited thereto.

Therefore, the transparent substrate is transferred with the ring-shaped photoresist pattern of the first mold, and may be one that the ring-shaped transparent protrusion is integrally formed with the transparent base having a transparent plate shape. As the transparent protrusion is formed by transferring the ring-shaped photoresist pattern of the first mold, the transparent protrusion may be the ring shape in which with respect to the diameter of the plate-type metal dot of 300 nm to 3 µm, an outer diameter of the ring is 70% to 200%, an inner diameter thereof is 5 to 80%, and a width thereof may be 2 to 48%. In this case, as described above, the siloxane-based elastomeric polymer may be used as the second mold and the transparent substrate is made of polyurethane having high elasticity and flexibility, and as a result the ring-shaped photoresist pattern having the foregoing dimension may be transferred so that the sharp corners of the photoresist pattern is smoothly curved. In this case, the inner diameter of the ring of the first mold ranges from 300 nm to 2 µm, preferably, 400 nm to 1.5 µm so that the whole bottom surface thereof may be concavely curved by the rounding of the corners while metal nanoparticles are easily carried.

In this case, the plurality of plate-type metal dots are arranged on the photo mask while being spaced apart from each other, and therefore the plurality of ring-shaped photoresist patterns arranged to be spaced apart from each other may be formed in the first mold. As the photoresist pattern is transferred to the transparent protrusion, the ring-shaped transparent protrusions are arranged to be spaced apart from each other, thereby forming an array.

When the ring-shaped transparent protrusions form the array, the transparent protrusions are preferably arranged to be spaced apart from each other to prevent the optical interference between the transparent protrusions from occurring and form the wells independent of each other. As the detailed and non-restrictive example, the transparent protrusions may be arranged in an M×N (M is a natural number of 2 or more and N is a natural number of 2 or more) matrix form while being spaced apart from each other and the interval between the transparent protrusions may range from several micro to hundreds of micro, specifically, 5 µm to 1 mm.

As described above, in the ring-shaped transparent protrusion, the bottom surface inside the ring may have the concavely curved shape. In detail, the bottom surface may have the concavely curved shape so that the center of the bottom surface is a bottom portion. The concavely curved shape is very advantageous to carry heterogeneous materials in the ring. In particular, when the metal nanoparticles generating the surface plasmon are carried in the ring, the metal nanoparticles are physically collected to the bottom portion of the bottom surface by the concavely curved shape and therefore the contact between the metal nanoparticles may occur. By doing so, the kind (physical contact between particles), position (bottom portion of the bottom surface), and density (the number of contact dots of particles controlled by the number of particles) of hot spot that may be strictly reproduced may be controlled only by the control of the number of metal nanoparticles only carried in the ring.

As described above, the method for manufacturing a transparent substrate according to the exemplary embodiment of the present invention may form the micro well providing analysis fields independent of each other and optically analyze in real time the object to be analyzed by the transparency. Further, as described below, the manufactured transparent substrate may be very effectively used as the surface enhanced Raman scattering substrate.

Manufacturing of Surface Enhanced Raman Scattering Substrate

The method for manufacturing a surface enhanced Raman scattering substrate includes positioning metal nanoparticles generating surface plasmons in a ring of a ring-shaped transparent protrusion of the transparent substrate manufactured by the foregoing method for manufacturing a transparent substrate.

In detail, the method for manufacturing a surface enhanced Raman scattering substrate according to an exemplary embodiment of the present invention includes: a) forming a photoresist layer satisfying the following Relational Expression 1 on a substrate; b) manufacturing a ring-shaped pattern by exposing the photoresist layer and developing the exposed photoresist layer, using a photo mask including a transparent base and a plate-type metal dot formed contacting a light emitting surface of the transparent base; c) manufacturing a second mold to which the ring-shaped pattern is reversely transferred by using a substrate on which the ring-shaped pattern is formed as a first mold; d) manufacturing the transparent substrate in which a ring-shaped transparent protrusion is integrally formed with a transparent base by filling a liquefied transparent resin in the second mold and curing the transparent resin and removing the second mold to transfer the ring-shaped pattern; and e) positioning metal nanoparticles generating surface plasmons in a ring of a ring-shaped transparent protrusion of the manufactured transparent substrate.

As known in the plasmonic field, the surface plasmon means the phenomenon that plasmon that is a collective motion of free electrons of the metal is formed by being concentrated on the surface of the metal structure by the interaction between metal that is a structure having the nano dimension and light. As the metal nanoparticles generating the surface plasmon, any metal nanoparticles known as generating the surface plasmon may be used. As the detailed example, the metal nanoparticles having the surface plasmon may be at least one or two materials selected from gold, silver, copper, lithium, aluminum, and an alloy thereof, but the present invention is not limited thereto.

The size of the metal nanoparticles may be carried in the micro well that is the ring-shaped transparent protrusion and when the plurality of metal nanoparticles are carried, may be appropriately controlled in consideration of the size of the micro well. As the detailed and non-restrictive example, the diameter of the metal nanoparticles ranges from 5 nm to 500 nm, specifically, 20 nm to 300 nm, but is not limited thereto.

To position the metal nanoparticles in the micro well that is the ring-shaped transparent protrusion, any method already known may be used. As an example, the metal nanoparticles may be carried in the micro well by drop casting, spin coating, gravity-driven nanoparticle printing, dipping, or the like. Preferably, the positioning of the metal nanoparticles in the micro well that is the ring-shaped transparent protrusion may include dipping the transparent substrate in a dispersion in which the metal nanoparticles are dispersed. In detail, the metal nanoparticles may be positioned in the micro well by a simple method for dipping the transparent substrate in the dispersion in which the metal nanoparticles are dispersed and then taking out the transparent substrate from the dispersion. The dipping method is a simple and cheap process and therefore may facilitate the construction of the manufacturing process, thereby saving production costs and improving productivity. Further, the number of metal nanoparticles positioned in the micro well may be easily controlled by controlling a concentration of the metal nanoparticles in the dispersion.

To effectively charge the metal nanoparticles in the dispersion in the micro well, upon the dipping, an angle of the transparent substrate and the surface of the dispersion may be maintained at 0 to 60°. That is, when the transparent substrate is dipped in the dispersion, the transparent substrate and the surface of the dispersion may be maintained in the state in which they are parallel with each other or may be maintained in the state in which the angle between the transparent base surface of the transparent substrate and the surface of the dispersion is inclined at about 60°.

As described above, as the transparent substrate is dipped in the dispersion in the state in which the angle of the transparent substrate and the surface of the dispersion is maintained at 0 to 60°, the metal nanoparticles may be effectively introduced into the micro well and the introduced metal nanoparticles may stably stay in the micro well.

When the metal nanoparticles are positioned in the micro well by using the dipping method, after the dipping is performed, a drying step of volatilizing and removing a dispersion medium of the dispersion of the metal nanoparticles may be further performed. The metal nanoparticles may have physically most stable arrangement by applying physical vibration or shock to the micro well (transparent substrate in which the metal nanoparticles are charged in the micro well) in which the metal nanoparticles are charged. Further, as the metal nanoparticles are positioned in the micro well and then the optical observation is made by the transparency of the transparent substrate, a step of measuring the number of metal nanoparticles positioned in each micro well and then sorting the micro wells in which the same number of metal nanoparticles are charged may be further performed. Upon substantially detecting a material to be detected, the micro wells in which the same number of metal nanoparticles is charged may be used as effective wells.

In the ring-shaped transparent protrusion, the bottom surface inside the ring may have the concavely curved shape and the hot spot may be formed between the metal nanoparticles by the curved shape of the bottom surface. That is, in the micro well that is the ring-shaped transparent protrusion, the bottom surface of the well may have the concavely curved shape and the metal nanoparticles are physically collected to a predetermined dot (bottom dot) by the curved shape, and as a result the hot spot between the metal nanoparticles may be formed. In this case, the bottom dot of the concavely curved bottom surface may coincide with the center of the well (ring).

The metal nanoparticles are physically collected to the bottom portion of the bottom surface by the concavely curved shape and as the contact between the metal nanoparticles occurs, the same kind of hot spots called the physical contact between the metal nanoparticles in each micro well may be formed. Further, as the number of contact dots between the metal nanoparticles is controlled by the number of metal nanoparticles, the number of hot spots in each micro well may be strictly and identically controlled. Further, as the metal nanoparticles are collected to the bottom portion of the bottom surface and the hot spot is formed by the contact between the nanoparticles, the accurate position of the hot spot may also be defined well.

As described above, the surface enhanced Raman scattering substrate manufactured by the manufacturing method according to the present invention may have the well defined structure in which the kind of hot spots, the number of hot spots, and the position of hot spots are controlled, such that the material to be detected may be reproducibly and reliably detected and may be detected with a fixed amount (absolute amount).

The surface of the metal nanoparticles dispersed in the dispersion may be formed with an acceptor which is specifically bonded to the material to be detected.

As the detailed example, the material to be detected may be a biochemical material, in which the biochemical material includes cell constituents, genetic materials, carbon compounds, metabolism of living bodies, material synthesis, material transportation, or organic matters affecting a signal transfer process. In detail, the biochemical material may include polymer organic matters, organic metal compounds, peptide, carbohydrate, protein, protein composite, lipid, metabolome, antigen, antibody, enzyme, substrate, amino acid, aptamer, sugar, nucleic acid, nucleic acid fragment, peptide nucleic acid (PNA), cell extract, or a combination thereof.

The specific binding between the acceptor and the material to be detected includes ionic bond, covalent bond, hydrogen bond, coordinate bond, or non-covalent bond. In detail, the acceptor may be a material that may be specifically bonded to the material to be detected by complementary bond, or the like between enzyme-substrate, antigen-antibody, protein-protein, or DNAs.

The present invention includes the surface enhanced Raman scattering substrate manufactured by the manufacturing method described above.

The surface enhanced Raman scattering substrate according to the present invention includes the transparent base having a transparent plate shape and the ring array in which the ring-shaped transparent protrusions integrated with the transparent base are arranged to be spaced apart from each other, in which the metal nanoparticles generating the surface plasmon may be positioned in the ring.

That is, the surface enhanced Raman scattering substrate according to the exemplary embodiment of the present invention may include the transparent base having the transparent plate shape, the ring-shaped transparent protrusions integrated with the transparent base, and the metal nanoparticles positioned in the ring-shaped transparent protrusions.

The ring-shaped transparent protrusion may be integrated with the transparent base and the plurality of transparent protrusions are arranged to be spaced apart from each other to form the array. As the detailed and non-restrictive example, the transparent protrusions may be arranged in an M×N (M is a natural number of 2 or more and N is a natural number of 2 or more) matrix form while being spaced apart from each other and the interval between the transparent protrusions may range from several micro to hundreds of micro, specifically, 1 μm to 1 mm.

The ring-shaped transparent protrusion and the transparent base may have the transparency to transmit visible light or light in near infrared ray region, in detail, may have light transmittance of 95% or more in a wavelength band ranging from 0.4 μm to 3 μm. The ring-shaped transparent protrusion and the transparent base may be made of at least one selected from acrylic resin, polycarbonate resin, acrylonitrile butadiene styrene resin, polyurethane resin, olefin-based resin, epoxy-based resin, melamine-based resin, and unsaturated polyester-based resin, preferably, high-elastic polyurethane resin as described above.

In the ring-shaped transparent protrusion, the outer diameter of the ring may range from 210 nm to 6 μm, the inner diameter of the ring may range from 15 nm to 2.4 μm, the width of the ring may range from 6 nm to 1.44 μm, the height of the ring (protruding height of the protrusion) may range from 50 nm to 500 nm. Preferably, the inner diameter of the ring may range from 300 nm to 2 μm□so that the metal nanoparticles are easily carried and the bottom surface of the ring-shaped transparent protrusion are curved on the whole.

The metal nanoparticles may be metal generating the surface plasmon and as the detailed example, may be at least one or two materials selected from gold, silver, copper, lithium, aluminum, and an alloy thereof, but the present invention is not limited thereto. The diameter of the metal nanoparticles may be appropriately controlled in consideration of the internal space of the ring-shaped transparent protrusion and as the detailed example, may range from 5 nm to 500 nm, specifically, 20 nm to 300 nm, but is not limited thereto.

The metal nanoparticles positioned in the ring of the ring-shaped transparent protrusion may be 1 to 20 and may be 2, 3, 4, 5, or 6 in the formation of the uniformly controlled hot spot. Further, for each transparent protrusion, the metal nanoparticles having the same number may be positioned in the transparent protrusions.

In the surface enhanced Raman scattering substrate according to the exemplary embodiment of the present invention, in the ring-shaped transparent protrusion, the bottom surface inside the ring may have the concavely curved shape and the hot spot may be formed between the metal nanoparticles by the curved shape of the bottom surface.

As the metal nanoparticles are physically collected to the bottom portion of the bottom surface by the concavely curved bottom surface and the contact between the metal nanoparticles occurs, the same kind of hot spots may be formed at the well defined position with the controlled density (the number of hot spots for each micro well).

The metal nanoparticles may be formed with an acceptor in which the surface thereof is specifically bonded to the material to be detected and the acceptor may be a material specifically bonded to the material to be detected by complementary bond, or the like between enzyme-substrate, antigen-antibody, protein-protein, or DNAs but is not limited thereto.

Figure 1:
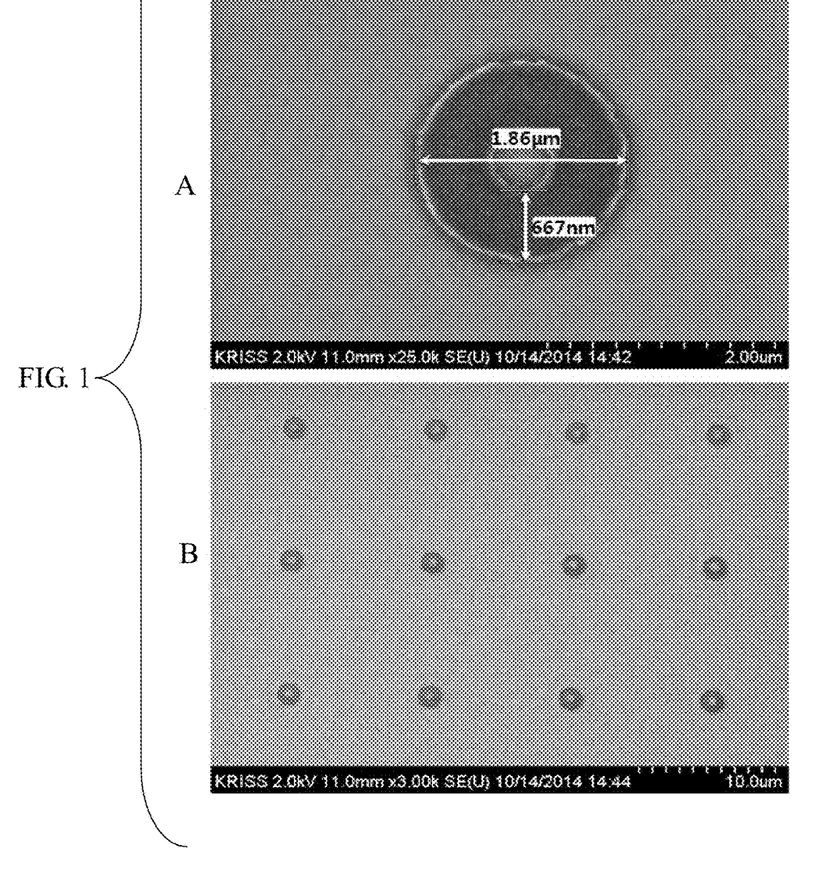
FIG. 1 is a scanning electron microscope photograph (high magnification observation photograph of FIG. 1A and low magnification observation photograph of FIG. 1B) obtained by observing a photoresist pattern of a first mold manufactured according to one exemplary embodiment of the present invention.

FIG. 1 is a scanning electron microscope photograph obtained by observing the manufactured first mold. In detail, by using the plate-type quartz as the transparent base, the photo mask in which a Cr plate (plate-type metal dot) having a height of 100 nm and a radius of 500 nm is regularly arranged on one surface of the transparent substrate at an interval of 10 μm and the protrusion is formed to form a gap (air gap) of 100 nm was used. It is a scanning electron microscope photograph obtained by observing the photoresist pattern manufactured by forming the positive photoresist layer having a thickness (m=4 in the above Relational Expression 1) of 420 nm on the base which is a silicon wafer (S1805), adheredly aligning the photo mask on the photoresist layer, irradiating the ultraviolet of 365 nm at a dose of 101 mJ/cm$^2$ thereto to perform the exposure, and then performing development (AZ300MIF) for 160 seconds.

As illustrated in FIG. 1, it may be appreciated that the photoresist may be patterned in the ring shape by using the mask in which the plate-type metal dot is only formed on the flat plate-like transparent base, not an expensive PSM and the single-layered micro ring type pattern having an outer diameter of 1.86 μm and a ring width of 667 nm may be manufactured.

Figure 2:
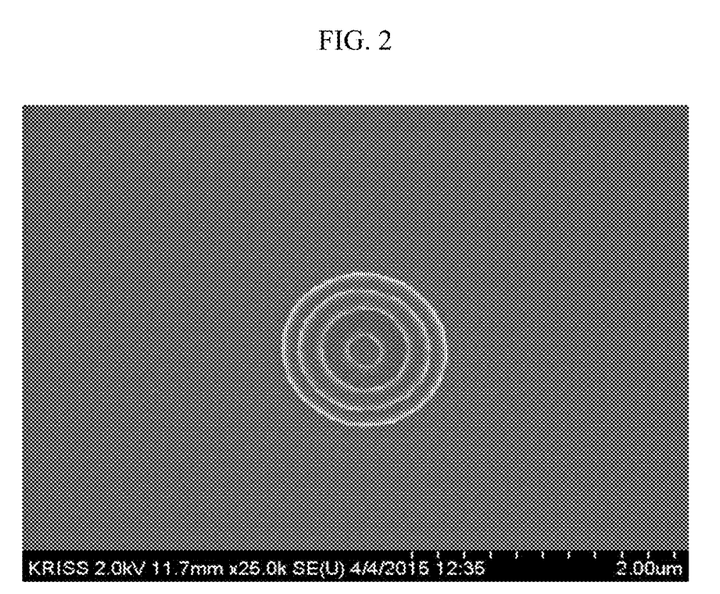
FIG. 2 is a scanning electron microscope photograph obtained by observing a photoresist pattern of a first mold manufactured according to another exemplary embodiment of the present invention.
Figure 3:
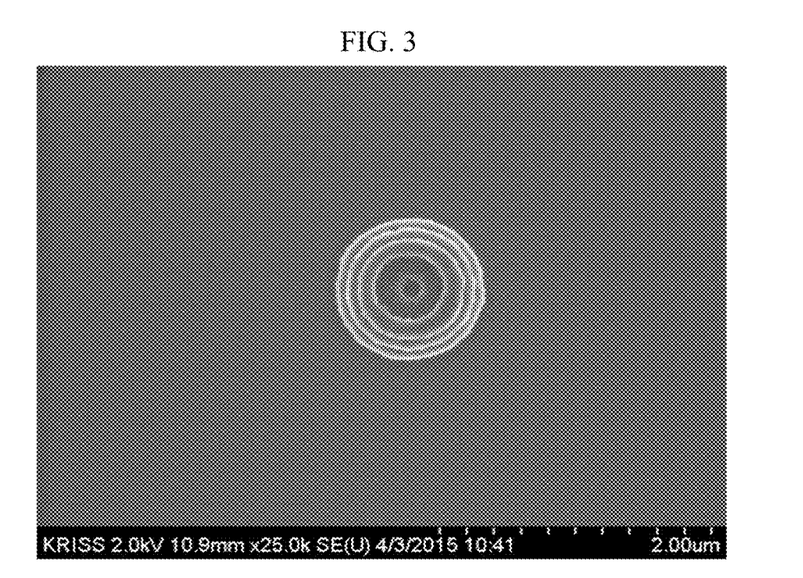
FIG. 3 is a scanning electron microscope photograph obtained by observing a photoresist pattern manufactured according to another exemplary embodiment of the present invention.

FIG. 2 is a scanning electron microscope photograph obtained by observing the photoresist pattern manufactured by the same method as the photoresist pattern observed in FIG. 1 and by performing the development for 62 seconds and FIG. 3 is a scanning electron microscope photograph obtained by observing the photoresist pattern manufactured by the same method as the photoresist pattern observed in FIG. 1 and by performing the development for 17 seconds.

As illustrated in FIGS. 2 and 3, it may be appreciated that the multi-layered ring pattern having the concentric structure and the outer diameter of the ring reduced upwardly may be manufactured by performing the exposure and then controlling the development time under the multi-layered ring manufacturing condition.

Further, as illustrated in FIGS. 1, 2, and 3, it may be appreciated that the ring type pattern having the single-layer, two-layer, or three-layer structure is manufactured by performing the exposure to form the exposed region as the multi-layered ring structure and then controlling only the development time.

Further, as can be appreciated from FIG. 3, it may be appreciated that by using the plate-type metal dot of which the diameter is 1000 nm, the ring pattern having an outer diameter of 955 nm and an inner diameter of 805 nm that is a size smaller than that of the plate-type metal dots may be manufactured.

Further, the photoresist pattern having the single-layered ring shape was manufactured by the same method as the photoresist pattern observed in FIG. 1 but as the result of performing the exposure so that the dose of irradiated light is 111 mJ/cm$^2$, it was confirmed that the photoresist pattern having the single-layered ring shape is manufactured independent of the development time.

Figure 4:
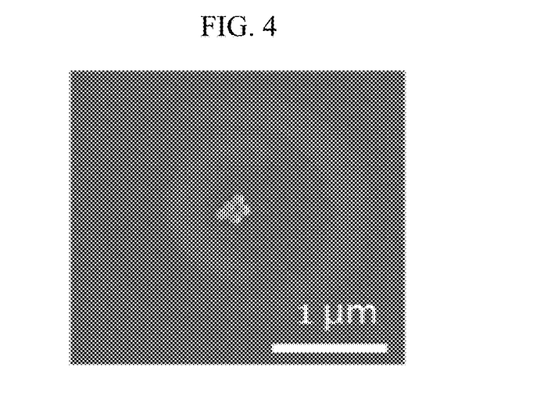
FIG. 4 is a scanning electron microscope photograph obtained by observing a surface enhanced Raman scattering substrate manufactured according to an exemplary embodiment of the present invention.

FIG. 4 is a scanning electron microscope photograph obtained by observing the manufactured surface enhanced Raman scattering substrate. In detail, the second mold that is a polydimethylsiloxane elastomeric polymer having the modulus of elasticity of about 1.7 MPa was manufactured by coating polydimethylsiloxane pre-polymer (Dow Corning, Sylgard® 184, mixture of pre-polymer with hardener at a mass ratio of 10:1 according to instructions) having hardenability on the first mold of FIG. 1, hardening the mixture at 70° C. for one hour, and then separating it. Next, the transparent substrate of polyurethane having a modulus of elasticity of about 1034 MPa was manufactured by coating polyurethane pre-polymer (Norland, NOA 61) having ultraviolet hardenability on the manufactured second mold, covering a glass substrate thereon, irradiating the polyurethane pre-polymer with ultraviolet rays of 32 mW/cm$^2$ to harden the polyurethane pre-polymer, and then separating the polyurethane pre-polymer. The transparent substrate in which the metal nanoparticles are carried in the ring-shaped protrusion was manufactured by dipping the manufactured transparent substrate of polyurethane in a dispersion of gold nanoparticles at an angle of 45°, the gold nanoparticles having a diameter of 100 nm and being dispersed at $5.6 \times 10^9$ numbers/ml and then lifting up the transparent substrate at 20 µm/s and drying it while maintaining the angle of 45°. It can be appreciated from FIG. 4 that the transparent substrate integrally formed with the ring-shaped protrusion to which the ring-shaped photoresist pattern of the first mold is transferred is manufactured, the corners may be curved by the elasticity, and the bottom surface in the ring may be concavely curved. Further, it can be appreciated that as the bottom surface is concavely curved, the gold nanoparticles carried in the ring are collected to the bottom portion of the concave floor and the physical contact between the particles may occur.

Figure 5:
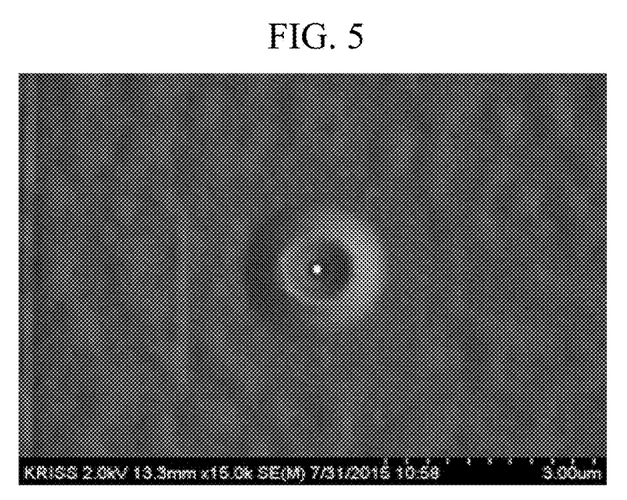
FIG. 5 is a scanning electron microscope photograph obtained by observing a surface enhanced Raman scattering substrate manufactured according to another exemplary embodiment of the present invention.
Figure 6:
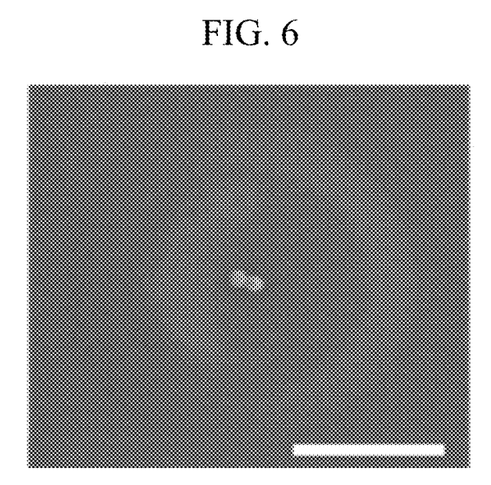
FIG. 6 is a scanning electron microscope photograph (scale bar=1 μm) obtained by observing a surface enhanced Raman scattering substrate manufactured according to another exemplary embodiment of the present invention.
Figure 7:
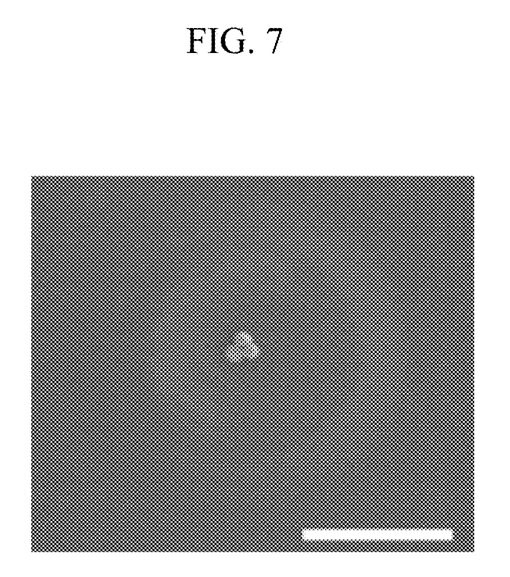
FIG. 7 is a scanning electron microscope photograph (scale bar=1 μm) obtained by observing a surface enhanced Raman scattering substrate manufactured according to another exemplary embodiment of the present invention.

FIGS. 5 to 7 are scanning electron microscope photographs obtained by observing other surface enhanced Raman scattering substrates which are manufactured like the surface enhanced Raman scattering substrate of FIG. 4 and are the scanning electron microscope photographs obtained by observing the surface enhanced Raman scattering substrate after one (FIG. 5), two (FIG. 6), or three (FIG. 7) metal nanoparticles are positioned on the manufactured transparent substrate to confirm that the gold nanoparticles are collected to the center of the concavely curved bottom surface and the physical contact between the metal nanoparticles is stably made. It can be appreciated from FIGS. 5 to 7 that the center of the ring becomes the bottom portion and the ring-shaped protrusions having the concavely curved bottom surface may be reproducibly formed and the physical contact between the metal nanoparticles is stably made independent of the number of metal nanoparticles by the concavely curved bottom surface.

Hereinabove, although the present invention has been described by specific matters, exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to these exemplary embodiments, but the claims and all of modifications equal or equivalent to the claims are intended to fall within the scope and spirit of the present invention.

The invention claimed is:

1. A method for manufacturing a transparent substrate, comprising:
    a) forming a photoresist layer satisfying the following Relational Expression 1 on a substrate;
    b) manufacturing a ring-shaped pattern by exposing the photoresist layer and developing the exposed photoresist layer, using a photo mask including a transparent base and a plate-type metal dot formed contacting a light emitting surface of the transparent base;
    c) manufacturing a second mold to which the ring-shaped pattern is reversely transferred by using a substrate on which the ring-shaped pattern is formed as a first mold; and
    d) manufacturing the transparent substrate in which a ring-shaped transparent protrusion is integrally formed with the transparent base by filling a liquefied transparent resin in the second mold and curing the transparent resin and removing the second mold to transfer the ring-shaped pattern
    wherein in the step b), the ring-shaped pattern is a single-layered ring shape or a multi-layered ring shape in which at least two rings are stacked, each ring of the multi-layered ring shape has a concentric structure, and an upper ring is positioned in a lower ring, in consideration of a projection image in a light irradiation direction, $$D=m*(\lambda/2n) \qquad \text{(Relational Expression 1)}$$

(D is a thickness of the photoresist layer, n is a refractive index of a photoresist, λ is a wavelength of light irradiated at the time of exposure, and m is a natural number of 1 or more).

2. The method of claim 1, wherein in the step b), the photo mask satisfies the following Relational Expression 2, and an interval between the photo mask and the photoresist layer satisfies the following Relational Expression 3

$$150\text{nm} \leq R \leq 1.5\text{µm}. \qquad \text{(Relational Expression 2)}$$

(In the above Relational Expression 2, R is a radius of the plate-type metal dot)

$$\text{Gap} \leq 200 \text{ nm} \qquad \text{(Relational Expression 3)}$$

(In the above Relational Expression 3, Gap is a spaced distance between the photo mask and the photoresist layer).

3. The method of claim 1, wherein in the step b), a ring-shaped pattern in which an outer diameter of a ring is 70% to 200% with respect to a metal dot diameter, an inner diameter thereof is 5 to 80% with respect to the metal dot diameter, and a width of the ring is 2 to 48% with respect to the metal dot diameter is manufactured by using the photo mask formed with the plate-type metal dot having a diameter of 300 nm to 3μm.

4. The method of claim 1, wherein the second mold is a siloxane-based elastomeric polymer.

5. The method of claim 4, wherein the transparent substrate is polyurethane.

6. The method of claim 5, wherein in the step d), the ring-shaped pattern in which a bottom surface inside the ring of the transparent protrusion is concavely curved is manufactured.

7. The method of claim 1, wherein in the step b), metal of the plate-type metal dot is at least one selected from transition metals including Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, and Au, post-transition metals including Al, Ga, In, Tl, Sn, Pb, and Bi, and metals including Li, Be, Na, Mg, K, Ca, Rb, Sr, Cs, and Ba.

8. The method of claim 1, wherein in the step b), light irradiated at the time of the exposure is ultraviolet (UV) and is irradiated at a dose of 90 to 110 mJ/cm$^2$.

9. The method for manufacturing a surface enhanced Raman scattering substrate, comprising:
    positioning metal nanoparticles generating surface plasmons in a ring of a ring-shaped transparent protrusion of the transparent substrate manufactured by the method for manufacturing a transparent substrate according to claim 1.

10. The method of claim 9, wherein in the ring-shaped transparent protrusion, a bottom surface inside the ring has a concavely curved shape and a hot spot is formed by physically contacting metal nanoparticles by the curved shape of the bottom surface.

11. The method of claim 9, wherein a surface of the metal nanoparticles is formed with an acceptor that is specifically bonded to a material to be detected.

12. The method of claim 9, wherein the positioning of the metal nanoparticles includes dipping the transparent substrate in a dispersion in which the metal nanoparticles are dispersed.

13. The method of claim 12, wherein upon the dipping, an angle between the transparent substrate and a surface of the dispersion is maintained at 0 to 60°.

14. A surface enhanced Raman scattering substrate, comprising:
    a transparent base having a transparent plate shape and an array in which a ring-shaped transparent protrusions integrally formed with the transparent base are arranged to be spaced apart from each other,
    wherein the inner diameter of the ring shape ranges from 300 nm to 2μm and metal nanoparticles generating surface plasmons are positioned in the ring,
    wherein in the ring-shaped transparent protrusion, a bottom surface inside the ring has a concavely curved shape and a hot spot is formed by physically contacting metal nanoparticles by the curved shape of the bottom surface.

15. The surface enhanced Raman scattering substrate of claim 14, wherein in the transparent protrusion of the array, the same number of metal nanoparticles are positioned in the ring.

16. The surface enhanced Raman scattering substrate of claim 14, wherein the number of metal nanoparticles positioned in the ring of the transparent protrusion is 2 to 6.

17. The surface enhanced Raman scattering substrate of claim 14, wherein a surface of the metal nanoparticles is formed with an acceptor that is specifically bonded to a material to be detected.

* * * * *